US011766235B2

(12) United States Patent
Nellur Prakash et al.

(10) Patent No.: US 11,766,235 B2
(45) Date of Patent: Sep. 26, 2023

(54) INTELLIGENT ULTRASOUND-BASED FERTILITY MONITORING

(71) Applicant: KONINKLIJKE PHILIPS N.V., Eindhoven (NL)

(72) Inventors: Sindhu Priyadarshini Nellur Prakash, Bangalore (IN); Ganesan Ramachandran, Bangalore (IN); Anumod Odungattu Thodiyil, Bangalore (IN); Sanjay Ramachandra Hegde, Bangalore (IN); Pallavi Vajinepalli, Bangalore (IN); Celine Firtion, Surat (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 139 days.

(21) Appl. No.: 16/755,213

(22) PCT Filed: Oct. 9, 2018

(86) PCT No.: PCT/EP2018/077444
§ 371 (c)(1),
(2) Date: Apr. 10, 2020

(87) PCT Pub. No.: WO2019/072827
PCT Pub. Date: Apr. 18, 2019

(65) Prior Publication Data
US 2020/0245968 A1    Aug. 6, 2020

Related U.S. Application Data

(60) Provisional application No. 62/570,951, filed on Oct. 11, 2017.

(51) Int. Cl.
*A61B 8/08* (2006.01)
*G16H 30/20* (2018.01)
(Continued)

(52) U.S. Cl.
CPC ............ *A61B 8/085* (2013.01); *A61B 8/465* (2013.01); *A61B 8/5223* (2013.01); *G06N 20/00* (2019.01);
(Continued)

(58) Field of Classification Search
None
See application file for complete search history.

(56) References Cited

U.S. PATENT DOCUMENTS 5,871,018 A * 2/1999 Delp .................... A61B 17/154
                                                      128/898
6,530,885 B1   3/2003 Entrekin et al.
(Continued)

FOREIGN PATENT DOCUMENTS

FR    2957514 A1 * 9/2011   ........... A61B 6/4417
JP    2013039156 A   2/2013
(Continued)

OTHER PUBLICATIONS

T. Chen, Wei Zhang, S. Good, K. S. Zhou and D. Comaniciu, "Automatic ovarian follicle quantification from 3D ultrasound data using global/local context with database guided segmentation," 2009 IEEE 12th International Conference on Computer Vision, 2009, pp. 795-802, doi: 10.1109/ICCV.2009.5459243 (Year: 2009).*
(Continued)

*Primary Examiner* — John Villecco
*Assistant Examiner* — Courtney Joan Nelson

(57) ABSTRACT

The present disclosure describes ultrasound imaging systems and methods configured to identify ovarian follicles by applying a neural network to pre-processed ultrasound image frames. Systems may include an ultrasound transducer configured to acquire echo signals responsive to ultrasound pulses transmitted toward a target region. One or more processors communicatively coupled with the ultra-
(Continued)

sound transducer may be configured to generate at least one image from the ultrasound echoes. A threshold may be applied to the image frame that differentiates pixels representative of an ovarian follicle present in the target region from other subject matter. The processors may apply a neural network to the thresholded image frame, in which the neural network determines the presence of the ovarian follicle in the thresholded image frame. The processors also may generate an indicator based on the presence of the ovarian follicle and display the indicator on a user interface.

19 Claims, 9 Drawing Sheets

(51) Int. Cl.
  *G16H 50/20* (2018.01)
  *G06N 20/00* (2019.01)
  *A61B 8/00* (2006.01)
  *G06T 7/00* (2017.01)

(52) U.S. Cl.
  CPC ........... *G06T 7/0012* (2013.01); *G16H 30/20* (2018.01); *G16H 50/20* (2018.01)

(56) References Cited

U.S. PATENT DOCUMENTS

| | | | |
|---|---|---|---|
| 8,425,425 B2 * | 4/2013 | Hagy ............... | A61B 5/062 600/461 |
| 2009/0093717 A1 | 4/2009 | Carneiro et al. | |
| 2011/0152684 A1 | 6/2011 | Altmann et al. | |
| 2013/0184584 A1 | 7/2013 | Berkey | |
| 2016/0113632 A1 | 4/2016 | Ribes et al. | |
| 2016/0292848 A1 * | 10/2016 | Plakas ............... | A61B 8/085 |
| 2016/0374644 A1 * | 12/2016 | Mauldin, Jr. ......... | A61B 8/085 600/424 |
| 2017/0061607 A1 | 3/2017 | Eskandari et al. | |
| 2017/0103518 A1 * | 4/2017 | Murphy ............... | A61B 8/08 |
| 2018/0140282 A1 | 5/2018 | Toyomura et al. | |
| 2018/0144471 A1 | 5/2018 | Govindjee et al. | |

FOREIGN PATENT DOCUMENTS

| | | | | |
|---|---|---|---|---|
| JP | 2017047082 A | | 3/2017 | |
| JP | 2018173507 A | | 11/2018 | |
| KR | 20150134299 A | * | 12/2015 | ............... A61B 8/14 |
| KR | 20160146487 A1 | * | 12/2016 | ............. A61B 8/483 |
| WO | 2018149765 A1 | | 8/2018 | |

OTHER PUBLICATIONS

S. Takemoto et al., "Semi-automated color segmentation from a biological cross-sectional image series: follicle segmentation from the equine ovary," 2004 IEEE International Conference on Systems, Man and Cybernetics (IEEE Cat. No. 04CH37583), 2004, pp. 3076-3081 vol. 4, doi: 10.1109/ICSMC.2004.1400811 (Year: 2004).*

Machine translation of FR-2957514-A1 (Year: 2011).*

B. Cahyono et al.: "An implementation of convolutional neural network on PCO classification based on ultrasound image", 2017 5th International Conference on Information and Communication Technology (ICoIC7), May 1, 2017, pp. 1-4 (Year: 2014).*

Machine translation of KR20160146487A1 (Year: 2016).*

Machine translation of KR20150134299A (Year: 2015).*

B. Purnama, U. N. Wisesti, Adiwijaya, F. Nhita, A. Gayatri and T. Mutiah, "A classification of polycystic Ovary Syndrome based on follicle detection of ultrasound images," 2015 3rd International Conference on Information and Communication Technology (ICoICT), 2015, pp. 396-401 (Year: 2015).*

Audibert et al: "A Global Perspective on Assisted Reproductive Technology Fertility Treatmetn: An 8-Country Fertility Specialist Survey"; Reprod Biol Endocrinol, 2015, vol. 13:133, 26 Page Document.

Cahyono et al: "An Implementation of Convolutional Neural Network on PCO Classification Based on Ultrsound Image"; 2017 Fifth International Conference, IEEE, 4 Page Document.

Cohen et al: "Count-Ception:Counting by Fully Convolutional Redundant Counting" Oct. 2017, 9 Page Document.

Donnadieu et al: Gynecologie-Obstetrique (Cahiers Des ECN), Elsevier-Masson Edition, Nov. 2006.

Hiremath et al:"Fuzzy Inference System for Follicle Detection in Ultrasound Images of Ovaries"; Soft Comput (2014), 18:1353-1362.

Hiremath et al: "Follicle Detection and Ovarian Classification in Digital Ultrasound Images of Ovaries"; Chapter 7 of "Advancements and Breakthroughs in Ultrasound Imaging"; Intech; Open Science/Open Minds, pp. 167-199.

Krizhevsky et al: "Imagenet Classification With Deep Convolutional Neural Networks"; Communications of the ACM, Jun. 2017, vol. 60, No. 6, pp. 84-90.

Lenic et al: "Segmentation of Ovarian Ultrasound Images Using Single Template Cellular Neural Networks Trained With Support Vector Machines": Twentieth IEEE International Symposium on Computer-Based Medical Systems (CFMS'07), 6 Page Document.

PCT/EP2018/077444 ISR & WO, dated Jan. 2019, 15 Page Document.

Isah, O.R. et al., "A Hybrid Model of PSO Algorithm and Artificial Neural Network for Automatic Follicle Classification", International Journal Bioautomation, 2017, vol. 21, No. 1, pp. 43-58. 43.

* cited by examiner

INTELLIGENT ULTRASOUND-BASED FERTILITY MONITORING

CROSS-REFERENCE TO PRIOR APPLICATIONS

This application is the U.S. National Phase application under 35 U.S.C. § 371 of International Application No. PCT/EP2018/077444, filed on Oct. 9, 2018, which claims the benefit of U.S. Provisional Patent Application No. 62/570,951, filed on Oct. 11, 2017. These applications are hereby incorporated by reference herein.

TECHNICAL FIELD

The present disclosure pertains to ultrasound systems and methods for identifying features in ultrasound images using a neural network. Particular implementations involve systems configured to identify ovarian follicles in ultrasound images by pre-processing the images and inputting them into a trained a neural network.

BACKGROUND

Infertility is a global problem estimated to impact 8% to 12% of couples at some point in their lives. The causes of infertility are widespread and include conditions such as polycystic ovarian syndrome (PCOS), decreased ovarian reserve, tubal factors, hypothyroidism, and various male conditions. To procreate, infertile patients may undergo, on average, three intra-uterine-insemination (IUI) treatment cycles and about 1.6 in vitro fertilization (IVF) treatment cycles, each cycle requiring about four to five visits to the fertility clinic. During each visit, ultrasound imaging may be performed to monitor fertility status, most often via trans-vaginal ultrasound scanning of the ovaries in search of ovarian follicles, the fluid-filled sacs from which mature eggs are released during ovulation. Follicular ultrasound scans may be performed serially throughout ovulation induction, especially during the follicular phase, e.g., the first two weeks of induction. Repeated scanning is often implemented to monitor follicular count and size over time, information which is then used to sort follicles according to development status and adapt patient-specific treatment plans as necessary. Generally, such monitoring may be performed on a regular basis until at least some of the follicles reach about 17-18 mm in diameter.

Monitoring follicular development is thus an iterative process often requiring frequent clinic visits. Such visits may be time-consuming and expensive, especially for rural patients located long distances from the nearest fertility clinic. A widespread shortage of ultrasound specialists trained to perform ovarian follicular scans only exacerbates access barriers for patients using artificial reproductive technology. To reduce the time spent at the clinic, as well as the associated travel and medical costs, remotely-implemented fertility monitoring and management systems may be desirable.

SUMMARY

The present disclosure describes systems and methods for monitoring fertility. In some examples, monitoring may be performed away from a clinic location, e.g., at a user's home. Methods described herein may be practiced by novice users untrained in ultrasound imaging techniques. The disclosed systems are configured to improve the accuracy and efficiency of ovarian follicle detection by first pre-processing ultrasound image data to accentuate ovarian follicles. Pre-processing may involve thresholding image frames to differentiate pixels representative of ovarian follicles from other features. The color or brightness of the pixels falling below and/or above the threshold value can be inverted to intensify the appearance of the follicles, thereby distinguishing them from other background features. After pre-processing, the disclosed ultrasound imaging systems may be configured to implement neural networks machine-trained to identify fertility status indicators, such as the ovarian follicles highlighted during pre-processing. Pre-processing the image data improves the ability of the neural network to positively identify follicles, and also reduces the processing required of the neural network, thereby enabling the system to be implemented on a remote point-of-care device in real time. While various features may be identified to monitor and manage fertility status according to the systems described herein, ovarian follicles are described for consistency. After ovarian follicle identification by a neural network, an indicator conveying the presence of the follicle(s) may be presented to a user via a user interface displaying live ultrasound images collected during an ultrasound scan. Instructions guiding the user through the ultrasound scan may also be generated and displayed or emitted by the user interface. Such instructions may assist the user in operation of the ultrasound imaging system to ensure that quality ultrasound images containing ovarian follicles are captured during a scan, even without confirmation or supervision by a trained specialist. Images containing the follicles may be transmitted to a specialist for additional analysis.

In accordance with some examples, an ultrasound imaging system may include an ultrasound transducer configured to acquire echo signals responsive to ultrasound pulses transmitted toward a target region. The system may also include one or more processors in communication with the ultrasound transducer. The processors may be configured to: generate at least one image frame from the ultrasound echoes; apply a threshold to the image frame that differentiates pixels representative of an ovarian follicle present in the target region from other subject matter in the target region; apply a neural network to the thresholded image frame, in which the neural network determines the presence of the ovarian follicle in the thresholded image frame; generate an indicator based on the determined presence of the ovarian follicle; and display the indicator on a user interface in communication with the processors.

In some examples, the processors may be further configured to generate and display an ultrasound image from the thresholded image frame on the user interface. In some embodiments, the processors may be further configured to intensify an appearance of the ovarian follicle in the thresholded image frame. In some examples, the threshold may be an Otsu threshold and the appearance of the ovarian follicle may be intensified by inverting a color of the pixels below and above the Otsu threshold. In some embodiments, the user interface may be configured to guide a user through an ultrasound scan in response to the indicator. In some embodiments, the user interface may be configured to guide the user through the ultrasound scan by providing an instruction to the user during the scan. The instruction may include at least one sensory cue. In some examples, the user interface may be configured to generate an ultrasound image from the thresholded image frame and send the ultrasound image to a remote receiver.

In some embodiments, the neural network may be a deep neural network (DNN) or a convolutional neural network (CNN). In some examples, the neural network may be a convolutional neural network (CNN) comprised of one or more convent layers and one or more fully connected layers. In some embodiments, the neural network may be operatively associated with a training algorithm configured to receive an array of training inputs and known outputs. The training inputs may include ovarian ultrasound image frames, and the known outputs may include ovarian ultrasound image frames comprising an ovarian follicle. In some examples, the neural network may be implemented, at least in part, in a computer-readable medium comprising executable instructions, which when executed by the processors coupled to the ultrasound transducer, cause the processors to perform a machine-trained algorithm to produce the indicator based on the acquired echo signals.

A method in accordance with the present disclosure may involve acquiring echo signals responsive to ultrasound pulses transmitted into a target region by a transducer operatively coupled to an ultrasound system; generating at least one image frame from the ultrasound echoes; applying a threshold to the image frame that differentiates pixels representative of an ovarian follicle present in the target region from other subject matter in the target region; applying a neural network to the thresholded image frame, in which the neural network determines the presence of the ovarian follicle in the thresholded image frame; generating an indicator based on the determined presence of the ovarian follicle; and displaying the indicator on a user interface.

In some examples, the method may further involve generating and displaying an ultrasound image from the thresholded image frame on the user interface. In some embodiments, the method may further involve inverting a color of the pixels falling above and below the threshold. In some examples, the method may further involve providing a user instruction responsive to the presence or absence of the ovarian follicle. The user instruction may include guidance for performing an ultrasound scan of an ovary.

In some embodiments, the neural network may be a convolutional neural network (CNN).

In some examples, the method may further involve training the neural network using ultrasound image frames containing an ovary. In some embodiments, the method may further involve generating an ultrasound image from the thresholded image frame and sending the ultrasound image to a clinician, where the clinician is located at a remote location. In some examples, the indicator may be updated in real time in response to movement of the transducer.

Any of the methods described herein, or steps thereof, may be embodied in non-transitory computer-readable medium comprising executable instructions, which when executed may cause a processor of a medical imaging system to perform the method or steps embodied herein.

DETAILED DESCRIPTION

Figure 1:
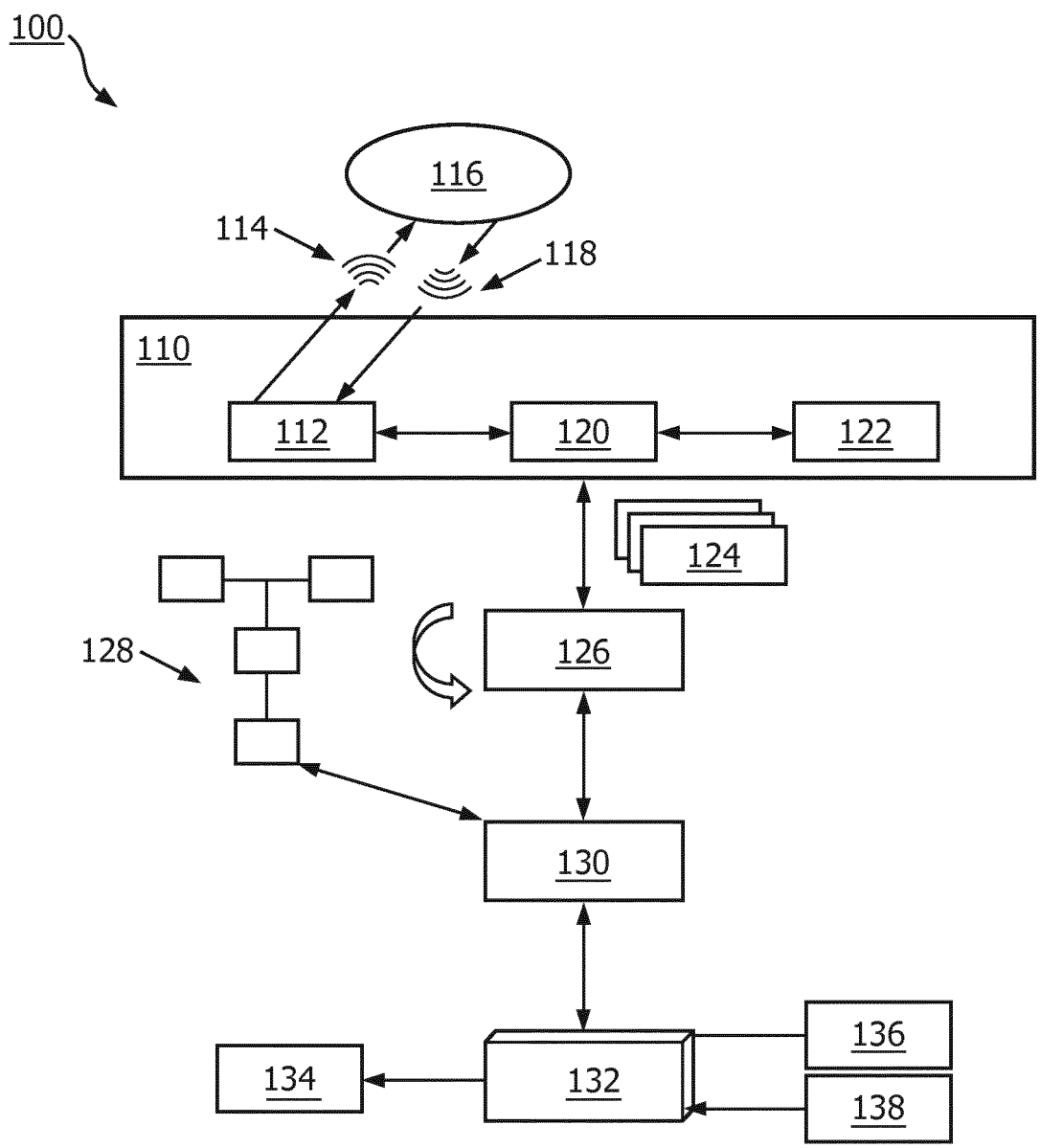
FIG. 1 is a block diagram of an ultrasound system in accordance with principles of the present inventions.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

An ultrasound system according to the present disclosure may utilize a neural network, for example a deep neural network (DNN), a convolutional neural network (CNN) or the like, to identify various features, e.g., ovarian follicles, detected via ultrasound imaging. In some examples, the neural network may be trained using any of a variety of currently known or later developed machine learning techniques to obtain a neural network (e.g., a machine-trained algorithm or hardware-based system of nodes) that is able to analyze input data in the form of ultrasound image frames and identify certain features, including the presence or absence of one or more ovarian follicles. Neural networks may provide an advantage over traditional forms of computer programming algorithms in that they can be generalized and trained to recognize data set features by analyzing data set samples rather than by reliance on specialized computer code. By presenting appropriate input and output data to a neural network training algorithm, the neural network of an ultrasound system according to the present disclosure can be trained to identify ovarian follicles and guide a user through an ultrasound scan of the ovaries based on the follicular identification.

An ultrasound system in accordance with principles of the present invention may include or be operatively coupled to an ultrasound transducer configured to transmit ultrasound pulses toward a medium, e.g., a human body or specific portions thereof, and generate echo signals responsive to the ultrasound pulses. The ultrasound system may include a beamformer configured to perform transmit and/or receive beamforming, and a display configured to display, in some examples, ultrasound images generated by the ultrasound imaging system. The ultrasound imaging system may include one or more processors and a neural network, which may be implemented in hardware and/or software components. The neural network can be machine trained to identify one or more bodily features, such as ovarian follicles, and output an indication of the presence and/or absence thereof.

The neural network according to the present disclosure may be hardware-(e.g., neurons are represented by physical components) or software-based (e.g., neurons and pathways implemented in a software application), and can use a variety of topologies and learning algorithms for training the neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in computer readable medium, and which when executed cause the processor to perform a machine-trained algorithm for identifying ovarian follicles within ultrasound images and, in some examples, output an indication of the presence or absence of the follicles. The ultrasound system may include a display or graphics processor, which is operable to arrange the ultrasound image and/or additional graphical information, which may include annotations, tissue information, patient information, indicators, and other graphical components, in a display window for display on a user interface of the ultrasound system. In some embodiments, the ultrasound images and tissue information, including information regarding the presence or absence of ovarian follicles, may be provided to a storage and/or memory device, such as a picture archiving and communication system (PACS) for reporting purposes or future machine training (e.g., to continue to enhance the performance of the neural network). In some examples, ultrasound images obtained during a scan may not be displayed to the user operating the ultrasound system, but may be selectively or automatically transmitted, e.g., over a communications network, to a specialist trained to interpret the information embodied in the images, e.g., a fertility specialist, an ultrasound specialist, a physician, or other clinician, thereby allowing a user to perform the ultrasound scans necessary for fertility monitoring, management, and/or diagnosis without visiting a clinic. The user operating the ultrasound imaging system and the specialist may be located in separate locations during an ultrasound scan, such that transmission of the ultrasound images and/or the information gleaned therefrom may occur over a geographical distance. In some examples, the user may be located at home, while the specialist is located at a clinic. The systems and methods described herein may be implemented to monitor infertility caused by a wide range of conditions. Female conditions may include ovulation disorders, e.g., PCOS and decreased ovarian reserve, tubal factors, e.g., hydrosalpinx and pelvic inflammatory disease, and hormonal factors, e.g., hypothyroidism and hyperprolactinemia. Male causes of infertility may also be amenable to the systems disclosed herein.

FIG. 1 shows an example ultrasound system according to principles of the present disclosure. The ultrasound system 100 may include an ultrasound data acquisition unit 110. The ultrasound data acquisition unit 110 may include an ultrasound probe which includes an ultrasound sensor array 112 configured to transmit ultrasound pulses 114 into a region 116 of a subject, e.g., lower abdomen, and receive ultrasound echoes 118 responsive to the transmitted pulses. As further shown, the ultrasound data acquisition unit 110 may include a beamformer 120 and a signal processor 122, which may be configured to generate a plurality of discrete ultrasound image frames 124 from the ultrasound echoes 118 received at the array 112. The system may also include a data processor 126, e.g., a computational module or circuitry, configured to pre-process the image frames 124 and implement a neural network 128. The neural network 128 may be configured to receive the image frames 124, either directly from the signal processor 122 or via the data processor 126, and determine a presence or absence of at least one ovarian follicle within each frame. In some examples, the system 100 also includes a display processor 130 coupled with the neural network 128 and a user interface 132. In some examples, the display processor 130 may be configured to generate ultrasound images 134 from the image frames 124 and generate an indicator 136 that conveys the presence or absence of an ovarian follicle within each of the image frames 124. The user interface 132 may be configured to display the ultrasound images 134 of the region 116 in real time as an ultrasound scan is being performed, along with the indicator 136. In some embodiments, the user interface 132 may not display ultrasound images, but may display the indicator 136, such that a user may not be able to see detected ovarian follicles, but will still be notified of their ultrasonic detection. The user interface 132 may also be configured to receive a user input 138 at any time before, during, or after an ultrasound scan. The configuration of the system 100 shown in FIG. 1 may vary. For example, the system 100 can be portable or stationary. Various portable devices, e.g., laptops, tablets, smart phones, or the like, may be used to implement one or more functions of the system 100. In examples that incorporate such devices, the ultrasound sensor array 112 may be connectable via a USB interface, for example.

The ultrasound data acquisition unit 110 may be configured to acquire ultrasound data from one or more regions of interest, which may include one or more ovaries. The ultrasound sensor array 112 may include at least one transducer array configured to transmit and receive ultrasonic energy. A variety of transducer arrays may be used, e.g., linear arrays, convex arrays, or phased arrays. The number and arrangement of transducer elements included in the sensor array 112 may vary in different examples. For instance, the ultrasound sensor array 112 may include a 1D or 2D array of transducer elements, corresponding to linear array and matrix array probes, respectively. The 2D matrix arrays may be configured to scan electronically in both the elevational and azimuth dimensions (via phased array beamforming) for 2D or 3D imaging.

A variety of users may handle and operate the ultrasound data acquisition unit 110. In some examples, the user may include a patient performing a self-evaluation. In various embodiments, the user may be untrained in clinical practices and/or ultrasound technology. Accordingly, the data acquisition unit 110 may part of a home monitoring system implemented by novice users.

As further shown in FIG. 1, the data acquisition unit 110 may also include a beamformer 120, e.g., comprising a microbeamformer or a combination of a microbeamformer and a main beamformer, coupled to the ultrasound sensor array 112. The beamformer 120 may control the transmission of ultrasonic energy, for example by forming ultrasonic pulses into focused beams. The beamformer 120 may also be configured to control the reception of ultrasound signals such that discernable image data may be produced and processed with the aid of other system components. The role of the beamformer 120 may vary in different ultrasound probe varieties. In some embodiments, the beamformer 120 may comprise two separate beamformers: a transmit beamformer configured to receive and process pulsed sequences of ultrasonic energy for transmission into a subject, and a separate receive beamformer configured to amplify, delay, and/or sum received ultrasound echo signals. In some embodiments, the beamformer 120 may comprise a microbeamformer operating on groups of sensor elements for both transmit and receive beamforming, coupled to a main beamformer which operates on the group inputs and outputs for both transmit and receive beamforming, respectively.

The signal processor 122 may be communicatively, operatively, and/or physically coupled with the sensor array 112 and/or the beamformer 120. In the example shown in FIG. 1, the signal processor 122 is included as an integral component of the data acquisition unit 110, but in other examples, the signal processor 122 may be a separate component. The signal processor 122 may be configured to receive unfiltered and disorganized ultrasound data embodying the ultrasound echoes 118 received at the sensor array 112. From this data, the signal processor 122 may continuously generate a plurality of ultrasound image frames 124 as a user scans the region 116.

The data processor 126, communicatively coupled with the signal processor 122, may perform one or more operations in addition to or in lieu of one or more operations performed by the signal processor 122. For example, the data processor 126 and/or the signal processor 122 may be configured to pre-process the image frames 124 and send or input the pre-processed images frames to the neural network 128. Pre-processing can enhance or intensify targeted features before input at the neural network to improve the sensitivity of the neural network 128 in identifying such features. The specific pre-processing steps performed by the data processor 126 may vary and may depend on the particular feature targeted by the system 100. For example, in embodiments involving ovarian follicle identification, pre-processing may be performed to intensify the appearance of ovarian follicles relative to the non-targeted features and background intensity in a given image frame 124. In an ultrasound image, ovarian follicles may be approximately elliptical in shape and dark relative to the surrounding features; however, other dark features or regions within the image may obscure the boundaries of individual follicles, making the follicles easy to miss or miscount when processed by the neural network 128. Thus, to improve the sensitivity of the neural network and reduce the processing required of the neural network, pre-processing may involve intensifying the image intensity characteristics of the follicle(s) against the background intensity of the ultrasound image data. Example methods of pre-processing may involve determining the intensity of the pixels comprising each ultrasound image frame and applying a brightness threshold to the pixels. In some embodiments, the brightness threshold may be an Otsu threshold, which reduces an image frame to a binary collection of pixels. All pixels above the Otsu threshold may be assigned a value, e.g., zero, while the remaining pixel values may be inverted. As a result, dark follicle regions may become brighter, e.g., nearly white, after thresholding, or vice versa, thereby increasing the visibility of any follicles present in a given image frame by sharpening the contrast between the follicles and the surrounding features. Employing a combination of pre-processing and neural network processing can optimize or at least improve ovarian follicle identification relative to embodiments relying on ovarian follicle identification performed via the neural network, only. In particular, pre-processing can increase the ability of the neural network 128 to positively identify ovarian follicles and significantly reduce the processing required of the neural network such that the entire follicle identification process can be performed in real time by a point-of-care device, as opposed to a hospital imaging system. In some examples, the sensitivity of follicle identification may be about 91% after applying the neural network to pre-processed images, compared to a sensitivity of about 85% achieved via direct application of the neural network to ultrasound images that have not been pre-processed.

In various embodiments, the neural network 128 may be embedded within or at least in communication with the signal processor 122 and/or the data processor 126. The neural network 128 may be configured to receive and input the ultrasound image frames 124, either directly from the signal processor 122 or after pre-processing performed by the data processor 126, signal processor, or both, and determine whether one or more ovarian follicles are present within each of the image frames 124. As discussed above, pre-processing the image frames 124 prior to input at the neural network 128 can increase the efficiency and accuracy of the neural network. In some examples, the neural network 128 may be a convolutional neural network (CNN) comprised of variously organized neural layers and sub-layers collectively trained to recognize ovarian follicles within ultrasound images. The neural network 128 may automatically detect the presence or absence of ovarian follicles within each received image frame 124, and may be implemented with two- or three-dimensional ultrasound imaging systems.

In some examples, the system 100 may be further configured to count the number of ovarian follicles identified in one or more image frames. Follicle counting may be performed using various system components, such as one or more processors, e.g., the data processor 126, and/or the neural network 128. The neural network 128 may be configured to count ovarian follicles according to various techniques, for example via the supervised learning concepts described in "Learning to count with deep object features" (Segui et al.), which is incorporated by reference in its entirety herein. Techniques described by Segui involve capturing discriminative information about ovarian follicles in a first processing stage and counting the number of follicles in a subsequent, fully-connected processing stage. In addition or alternatively, the neural network 128 may be configured to count ovarian follicles according to the techniques described in "Count-ception: Counting by Fully Convolutional Redundant Counting" (Cohen et al.), which is also incorporated by reference in its entirety herein. The methods disclosed by Cohen involve redundant follicle counting techniques that merge the concepts described by Segui with object density mapping. In some implementations, one or more processors may be configured to count follicles by performing image segmentation counting techniques on or more selected image frames from the neural network 128 that include at least one ovarian follicle, for example as described in European Patent Application No. 17305188.9 as filed on 17 Feb. 2017, which is also incorporated by reference in its entirety herein. Such image segmentation techniques may involve automated segmentation of follicles detected in 2-D ultrasound image frames to determine the average diameter of each follicle. In various embodiments, one or more additional or alternative follicle counting techniques may be employed, the results of which may be displayed or otherwise communicated to a user or a remotely-located clinician.

The display processor 130 communicatively coupled with the neural network 128 may be configured to generate an indicator 136 based on the determination made by the neural network 128. For example, the indicator 136 may indicate the presence or absence of at least one ovarian follicle. Upon receiving the ultrasound images 134 and/or the indicator 136, the user interface 132 may then display the images and/or indicator. The indicator 136 may be displayed concurrently with, e.g., superimposed on top of or next to, the ultrasound images 134 in real time as the images are obtained. Accordingly, the indicator 136 may instantly notify the user of the presence or absence of one or more ovarian follicles. In some examples, the indicator 136 may comprise a sensory cue that is not be visibly displayed, such as a vibration of the ultrasound probe or an audible cue emitted from speakers coupled with the ultrasound system 100. The indicator 136 may also comprise a light that turns on and off or changes color. For example, the presence of an ovarian follicle may be indicated via a green light, while the absence of an ovarian follicle may be indicated via a red light or an absence of light. In some embodiments, the indicator 136 may be displayed without the concurrent display of ultrasound images. The particular nature of the indicator 136 is not critical, provided the indicator notifies the user of the presence or absence of ovarian follicles.

In some examples, the user interface 132 may be further configured to guide or assist a user through an ultrasound scan. Such guidance may be responsive to the indicator 136 generated by the neural network 128 and the display processor 130. For example, the user interface 132 may provide a first instruction to the user in response to receiving an indicator 136 conveying the presence of an ovarian follicle, and in response to receiving an indicator 136 conveying the absence of an ovarian follicle, may provide a second, different instruction to the user. Such instructions may prompt the user to perform the ultrasound scan in a particular manner that ensures all ovarian follicles, if present, are detected during the scan. Instructions may include directional commands, e.g., "Move ultrasound probe laterally." Instructions may also include technique-based commands, e.g., "Move ultrasound probe slower"; "Slow down"; "Stop"; "or "Continue." In some examples, the instructions may command the user to hold an ultrasound probe steady at one location the moment an ovarian follicle is detected, thus ensuring that at least one image of the follicle is captured. Instructions may also prompt the user to make slight adjustments to the position and/or orientation of the ultrasound probe the moment an ovarian follicle is detected, thereby increasing the likelihood that the image clarity of the follicle is sufficient for subsequent analysis by a specialist viewing the image. An instruction may inform the user that a scan is complete, for example upon successful identification of one or more ovarian follicles.

Figure 2:
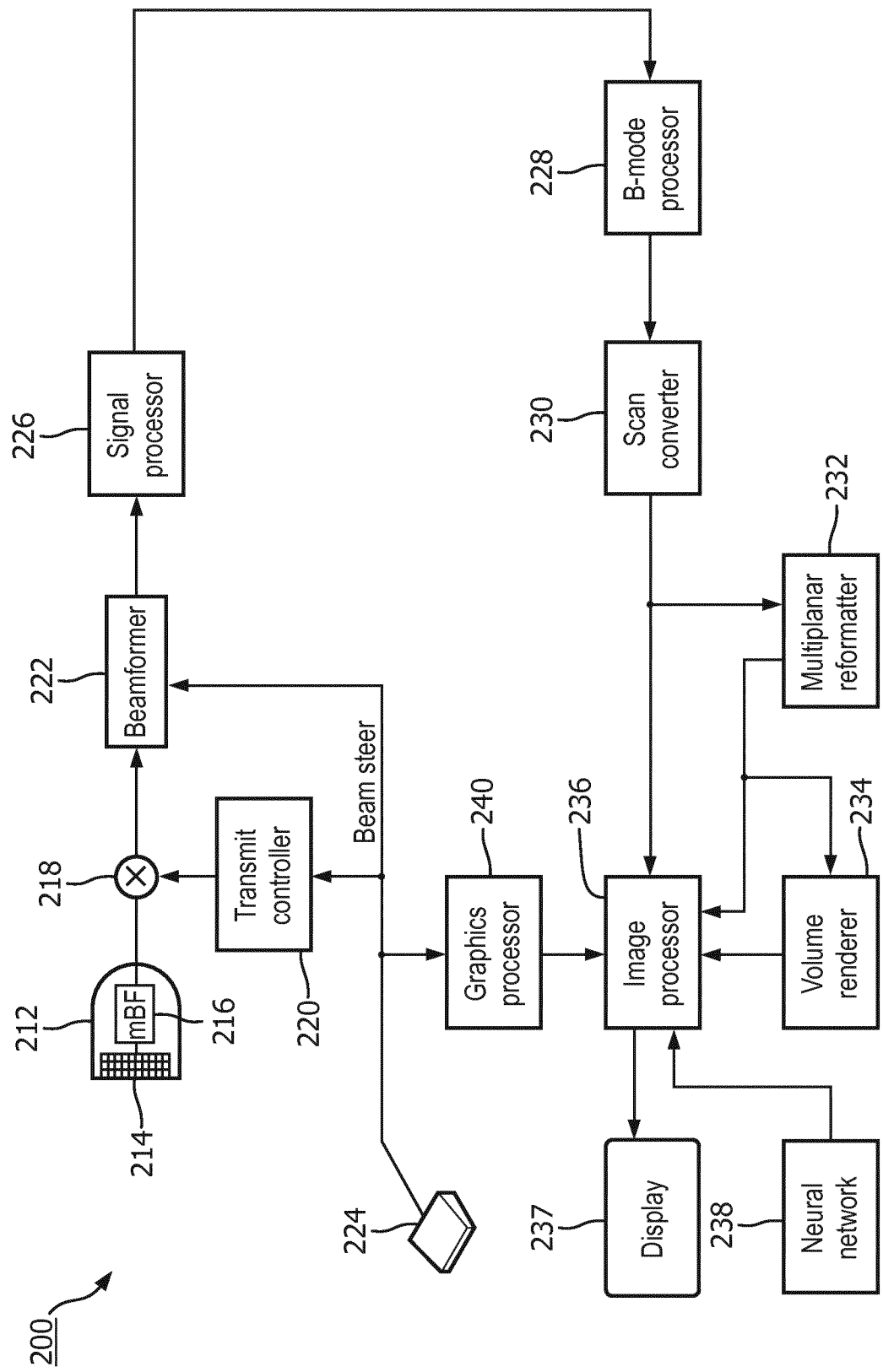
FIG. 2 is a block diagram of another ultrasound system in accordance with principles of the present inventions.

FIG. 2 is a block diagram of another ultrasound system 200 in accordance with principles of the present inventions. One or more components shown in FIG. 2 may be included within a system configured to identify ovarian follicles within a region of a subject, provide an indication of the presence or absence of the ovarian follicles, guide a user operating the system through an ultrasound scan in search of such follicles, and/or transmit one or more ultrasound images containing ovarian follicles to a specialist. For example, any of the above-described functions of the signal processor 122 may be implemented and/or controlled by one or more of the processing components shown in FIG. 2, including for example, signal processor 226, B-mode processor 228, scan converter 230, multiplanar reformatter 232, volume renderer 234 and/or image processor 236.

In the ultrasonic imaging system of FIG. 2, an ultrasound probe 212 includes a transducer array 214 for transmitting ultrasonic waves into a region containing the ovaries and receiving echo information responsive to the transmitted waves. In various embodiments, the transducer array 214 may be a matrix array or a one-dimensional linear array. The transducer array 214 may be coupled to a microbeamformer 216 in the probe 212 which may control the transmission and reception of signals by the transducer elements in the array. In the example shown, the microbeamformer 216 is coupled by the probe cable to a transmit/receive (T/R) switch 218, which switches between transmission and reception and protects the main beamformer 222 from high energy transmit signals. In some embodiments, the T/R switch 218 and other elements in the system can be included in the transducer probe rather than in a separate ultrasound system component. The transmission of ultrasonic beams from the transducer array 214 under control of the microbeamformer 216 may be directed by the transmit controller 220 coupled to the T/R switch 218 and the beamformer 222, which receives input, e.g., from the user's operation of the user interface or control panel 224. A function that may be controlled by the transmit controller 220 is the direction in which beams are steered. Beams may be steered straight ahead from (orthogonal to) the transducer array, or at different angles for a wider field of view. The partially beamformed signals produced by the microbeamformer 216 are coupled to a main beamformer 222 where partially beamformed signals from individual patches of transducer elements are combined into a fully beamformed signal.

The beamformed signals may be communicated to a signal processor 226. The signal processor 226 may process the received echo signals in various ways, such as bandpass filtering, decimation, I and Q component separation, and/or harmonic signal separation. The signal processor 226 may also perform additional signal enhancement via speckle reduction, signal compounding, and/or noise elimination. In some examples, the signal processor 226 may perform one or more of the image frame pre-processing steps described above to enhance the appearance of the ovarian follicles included in a given image. In some examples, data generated by the different processing techniques employed by the signal processor 226 may be used by a data processor and/or a neural network to identify one or more ovarian follicles. The processed signals may be coupled to a B-mode processor 228, which may employ amplitude detection for imaging structures in the body, including the ovaries and any follicles in proximity thereto, for example. The signals produced by the B-mode processor 228 may be coupled to a scan converter 230 and a multiplanar reformatter 232. The scan converter 230 may arrange the echo signals in the spatial relationship from which they were received in a desired image format. For instance, the scan converter 230 may arrange the echo signals into a two dimensional (2D) sector-shaped format. The multiplanar reformatter 232 may convert echoes which are received from points in a common plane in a volumetric region of the body into an ultrasonic image of that plane, as described in U.S. Pat. No. 6,443,896 (Detmer). In some examples, a volume renderer 234 may convert the echo signals of a 3D data set into a projected 3D image as viewed from a given reference point, e.g., as described in U.S. Pat. No. 6,530,885 (Entrekin et al.). The 2D or 3D images may be communicated from the scan converter 230, multiplanar reformatter 232, and volume renderer 234 to an image processor 236 for further enhancement, buffering and/or temporary storage for display on an image display 237. Prior to their display, the images may be pre-processed to highlight ovarian follicles and a neural network 238 may be implemented to identify whether each image contains one or more ovarian follicles. In embodiments, the neural network 238 may be implemented at various processing stages, e.g., prior to the processing performed by the image processor 236, volume renderer 234, multiplanar reformatter 232, and/or scan converter 230. A graphics processor 240 can generate graphic overlays for display with the ultrasound images. These graphic overlays may contain, e.g., standard identifying information such as patient name, date and time of the image, imaging parameters, and the like, and also various outputs generated by the neural network 238, such as one or more indicators conveying the presence or absence of ovarian follicles. Graphic overlays may also include visual instructions, e.g., text and/or symbols, for guiding a user of the system 200 through an ultrasound scan. In some examples, the graphics processor may receive input from the user interface 224, such as a typed patient name or confirmation that an instruction displayed or emitted from the interface has been acknowledged by the user of the system 200. The user interface 224 may also receive input prompting adjustments in the settings and/or parameters used by the system 200, input requesting additional instructions or assistance for performing an ultrasound scan, and/or input requesting that one or more ultrasound images be saved and/or transmitted to a remote receiver. The user interface may also be coupled to the multiplanar reformatter 232 for selection and control of a display of multiple multiplanar reformatted (MPR) images.

Figure 3:
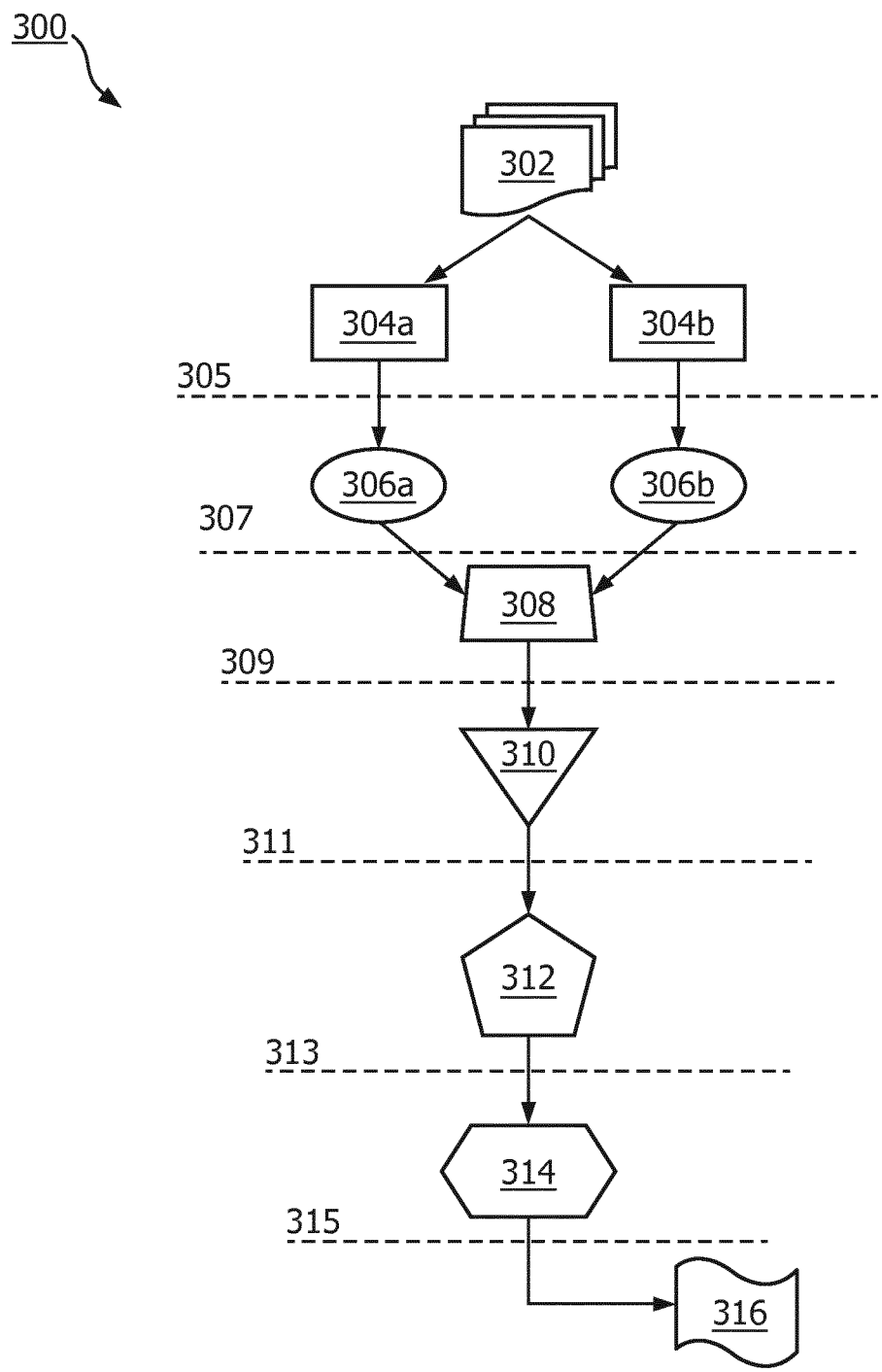
FIG. 3 is a block diagram of a convolutional neural network trained to identify ovarian follicles in ultrasound images in accordance with principles of the present inventions.

FIG. 3 is a block diagram of a neural network 300 trained to identify ovarian follicles in ultrasound image data according to principles of the present inventions. In the example shown, the neural network 300 is a convolutional neural network (CNN). In some embodiments, the neural network 300 may be a deep-learning or simply deep neural network (DNN) and/or an adaptive neural network. In some examples, a DNN, such as a deep convolutional neural network (deep CNN), also referred to as a fully convolutional network (FNC), may also be used to identify the presence of ovarian follicles within ultrasound images. The network architecture shown in FIG. 3, which is customized for performing ovarian follicle identification in pre-processed ultrasound images, represents only one example of the arrangement of neural layers and sub-layers, as well as the connectivity therebetween, which may be implemented according to embodiments of the present invention. For example, the number of convnet layers and/or fully-connected layers may be greater for identifying ovarian follicles in ultrasound images that have not been pre-processed. Likewise, the number of convnet layers and/or fully connected layers may be decreased for extensively pre-processed images.

The CNN shown in FIG. 3 is trained to receive an input 302 in the form of an ultrasound image frame, which may be pre-processed prior to arriving at the neural network. The input 302 may be received by two sets of convolutional neurons 304a, 304b arranged in parallel within a first convnet layer 305, which may be referred to as the "input layer." In some examples, the first convnet layer 305 may be trained to recognize the edges and/or intensity levels of various features within each received image frame. After processing by the first convnet layer 305, processing may continue in two more sets of convolutional neurons 306a, 306b arranged in parallel within a second convnet layer 307, which may be trained to separate ovarian follicles from other features having similar intensity levels. An additional set of convolutional neurons 308 in a third convnet layer 309 may be coupled to each set of convolutional neurons 306a, 306b from the preceding convnet layer 307. The third convnet layer 309 may be trained to highlight or otherwise emphasize the follicle(s) identified in the second convnet layer 307. Each convnet layer shown in FIG. 3 may include one or more sub-layers, e.g., a convolutional sub-layer, a normalization sub-layer, and/or a pooling sub-layer.

The convnet layers may be followed by three sets of fully-connected neurons 310, 312, 314 arranged in fully-connected layers 311, 313 and 315, respectively. Each set of fully connected neurons may be fully connected to the neural layers preceding and following it. From the last set of fully-connected neurons 314, an output 316 may be produced. For this reason, the last fully-connected layer 315 may also be referred to as the "output layer" in some examples. The output 316 may include an indication of the presence or absence of one or more ovarian follicles present within the original input 302. The output 316 may be coupled to a display processor, e.g., the display processor 130 shown in FIG. 1, which may convert the indication into an indicator configured for display on a user interface, for instance.

The neural network 300 may be implemented, at least in part, in a computer-readable medium comprising executable instructions, which when executed by a processor, such as data processor 126, coupled to an ultrasound transducer, may cause the processor to perform a machine-trained algorithm to produce the indicator of the presence or absence of an ovarian follicle based on the acquired echo signals. The neural network 300 may be configured to operate on feature detection and trained specifically to identify ovarian follicles. To train the neural network 300, training sets which include multiple instances of input arrays and output classifications may be presented to the training algorithm(s) of the neural network 300 (e.g., AlexNet training algorithm, as described by Krizhevsky, A., Sutskever, I. and Hinton, G. E. "ImageNet Classification with Deep Convolutional Neural Networks," NIPS 2012 or its descendants). In the training data sets, the input data may include ultrasound images generated via IUI and IVF monitoring ovarian scans, and the output data may include known features contained within the ultrasound images, e.g., ovarian follicles. In various examples, the input data may include ultrasound image frames that contain one or more ovarian follicles, and ultrasound image frames that do not contain ovarian follicles. In some embodiments, the output of the training process may be a set of weights, which may be used by the neural network 300 during operation. In some embodiments, the input and output data of the training data sets may be acquired by an ultrasound imaging system which has components for conventional ultrasound imaging. The ultrasound imaging system configured to implement the neural network 300 may include conventional beamforming, signal, and imaging processing components such that it may be used, when operated in a conventional mode, to acquire additional input and output data sets for use as training sets to the training algorithm.

A neural network training algorithm associated with the neural network 300 may be presented with thousands or even millions of training data sets in order to train the neural network to identify ovarian follicles within ultrasound images of the ovaries. For example, the weights of the CNN may be trained using 30 epochs, each epoch representing a single pass through a training set, and around 70,000 ultrasound images of IUI and IVF monitoring ovarian scans. The illustration of the neural network 300 shown in FIG. 3 is a simplified representation. In some examples, the neural network 300 may comprise hundreds of thousands to millions of neurons or nodes and connections therebetween. The signals and state of the artificial neurons in a neural network 300 may be real numbers, e.g., between 0 and 1, and a threshold function or limiting function may be associated with each connection and/or node itself, such that the signal must equal or exceed the threshold/limit before propagating. Once the neural network 300 is trained and fixed, a deep learning library compatible with the Android® operating system, for example, may be used to implement the trained CNN model.

Figure 4A:
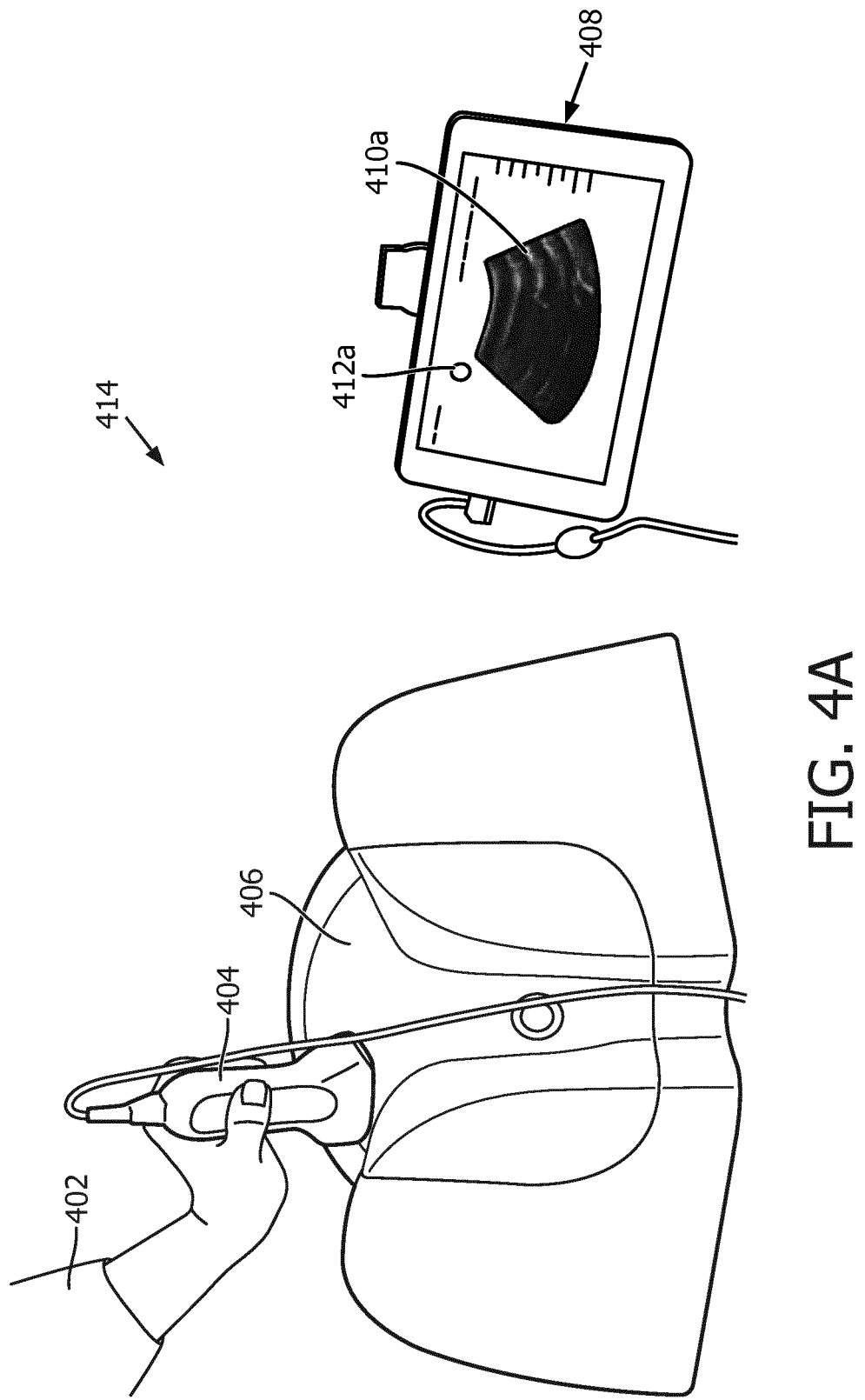
FIG. 4A is a photograph of an ultrasound scan being performed and a corresponding ultrasound image produced in accordance with principles of the present inventions.

FIG. 4A is a photograph of an ultrasound scan being performed according to the systems and methods disclosed herein. As shown, a user 402 may manipulate a handle-held ultrasound probe 404 to scan a region 406 of a subject, which may span the lower abdomen. The probe 404 may be coupled to a user interface 408, which in some examples may be configured to display a live ultrasound image of the scanned region. In the specific example shown, the current ultrasound image 410a does not contain ovarian follicles. Accordingly, the user interface 408 may display a negative indicator 412a, or no indicator at all, conveying the absence of ovarian follicles within the image. Upon movement of the probe 404, the indicator 412a may disappear or change due to the discovery of one or more ovarian follicles within a subsequently displayed image. Together, the probe 404 and the user interface 408 may comprise a mobile ultrasound imaging system 414 configured to monitor the fertility status of a patient.

Figure 4B:
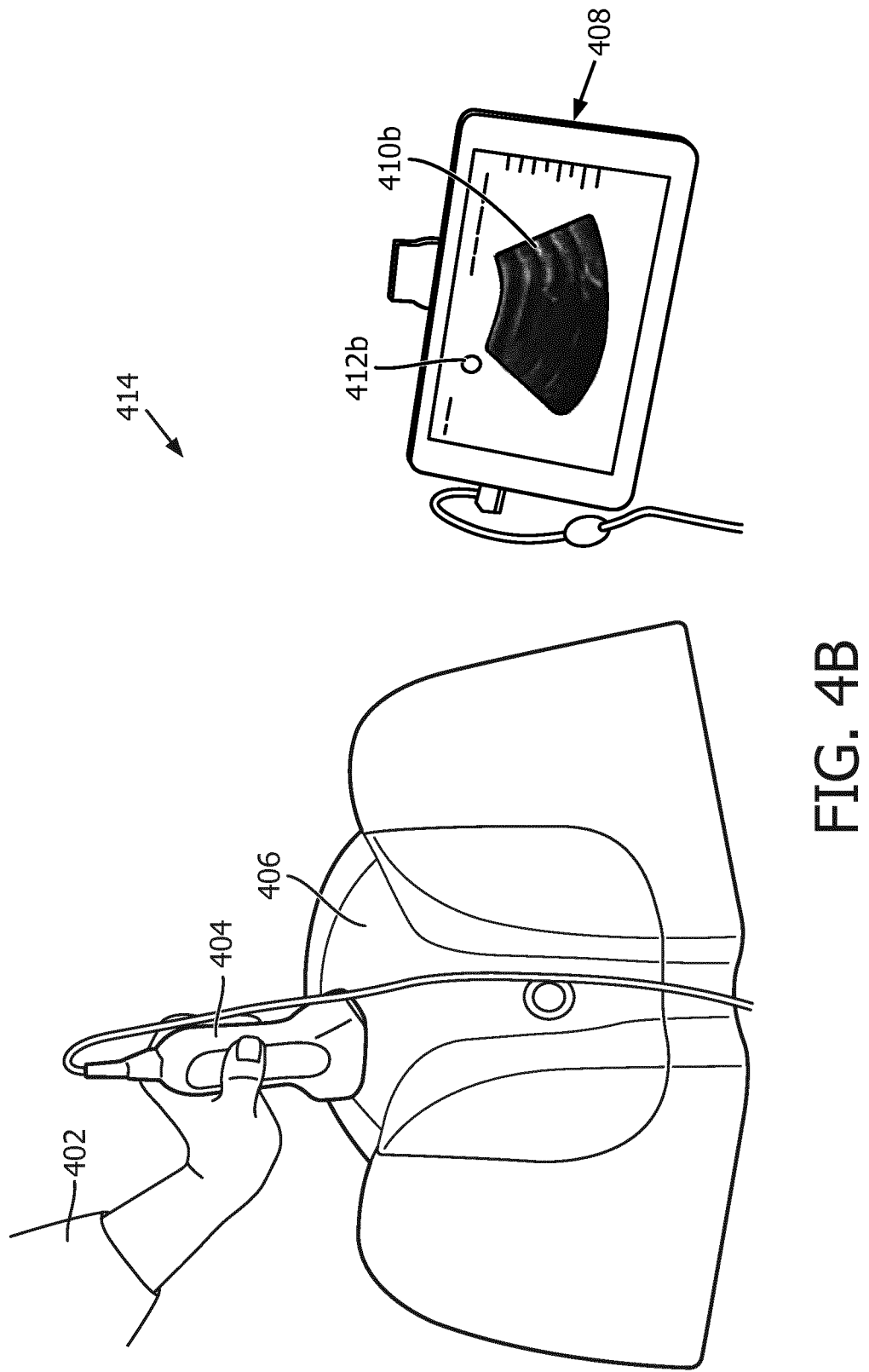
FIG. 4B is another photograph of an ultrasound scan being performed and a corresponding ultrasound image produced in accordance with principles of the present inventions.

FIG. 4B is another photograph of an ultrasound scan being performed according to the systems and methods disclosed herein. As shown, movement of the probe 404 may generate a different ultrasound image 410b that does contain at least one ovarian follicle, thereby prompting the system to generate and display a positive indicator 412b of the presence of the follicle. The difference between the negative and positive indicators may vary. For example, the indicators may be differentiated based on color, shape, and/or brightness. In some examples, identification of one or more follicles may indicate to the user 402 that the scan is done correctly.

The system 414 shown in FIGS. 4A and 4B may be adapted specifically for remote usage, e.g., within the home of the user 402. For every ultrasound image generated by the probe 404, background intelligence comprised of a neural network running within the system 414 may detect the absence or presence of ovarian follicles and instantly notify the user 402 of the same. In embodiments, the system 414 may be configured to guide and/or assist the user 402 through an ultrasound scan by providing periodic instructions to the user during the scan. The instructions may include various sensory cues. For example, the instructions may include audio cues emitted through a speaker, such as a plurality of sounds, beeps or verbal instructions. In addition or alternatively, instructions may include readable textual cues displayed on the user interface 408, and or other sensory cues, e.g., vibration of the probe 404.

After or simultaneously with displaying the images and/or indicator(s) to the user 402, a component of the system 414 may be configured to automatically store in memory and/or send ultrasound images or image data to a remote receiver for further analysis by a specialist. The specialist may analyze the received information at various times from various locations. In some examples, only the image data associated with a positive indicator, such as indicator 412b, may be automatically stored and/or sent to the remote receiver such that available storage space is preserved and/or a user at the receiving end, e.g., clinician, does not have to sort through a plurality of images to eliminate those containing zero follicles or follicles lacking clarity. In some embodiments, image transmission may be directed by the user 402, such that the user may, after performing a successful scan in which ovarian follicles are identified, send select ultrasound images or image data to the remote receiver. In some embodiments, the user 402 may use the system 414 for the first time without supervision or in-person training. The system 414 may be implemented in various locations, e.g., separate from a hospital or clinic, and may thus provide an at-home fertility-monitoring solution.

Figure 5:
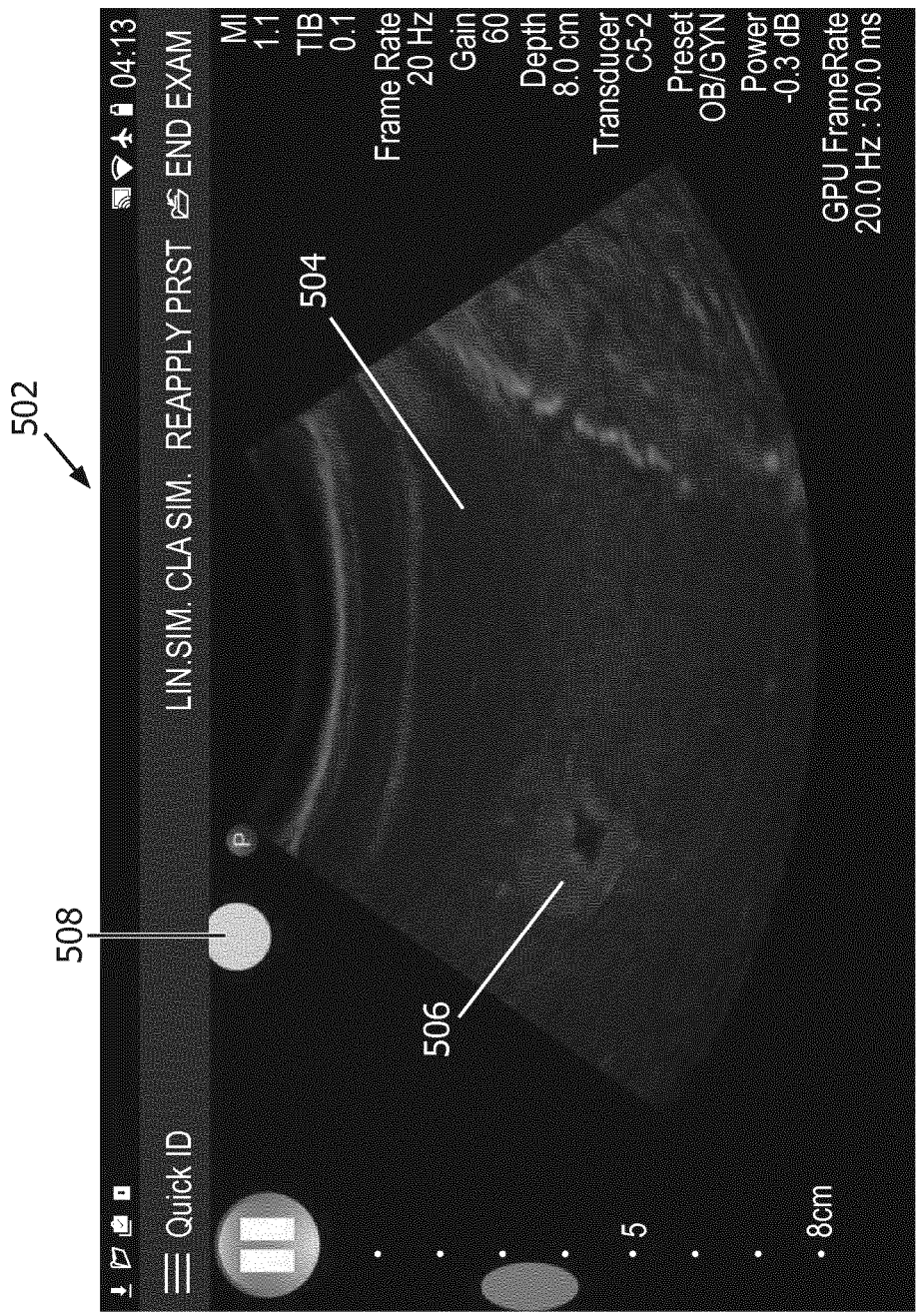
FIG. 5 is a photograph of an ultrasound image and ovarian follicle indicator displayed on a user interface in accordance with principles of the present inventions.

FIG. 5 is a photograph of an ultrasound image generated in accordance with the systems and methods disclosed herein. As shown, a user interface 502 may be configured to display a live ultrasound image 504 generated by an ultrasound transducer coupled with one or more processors configured to pre-process the image data and implement a trained neural network. Within the particular image shown, an ovarian follicle 506 is visible. Accordingly, a positive indicator 508 is also displayed on the user interface 502. The positive indicator 508 shown in this particular example consists of a circular dot displayed adjacent to the ultrasound image 504. The dot may be green to indicate follicular presence and switch to red to indicate follicular absence, but the color may vary in examples. In other embodiments, the indicator 508 may comprise a wide range of sensory cues, e.g., visual text or symbols, audible sounds, and/or vibrations conveyed at the user interface 502 or other system components, such as the ultrasound probe. In some examples, the user interface 502 may also be configured to display various follicular statistics. For example, the number and/or dimensions of the ovarian follicle(s) present within a given ultrasound image may be displayed.

Figure 6A:
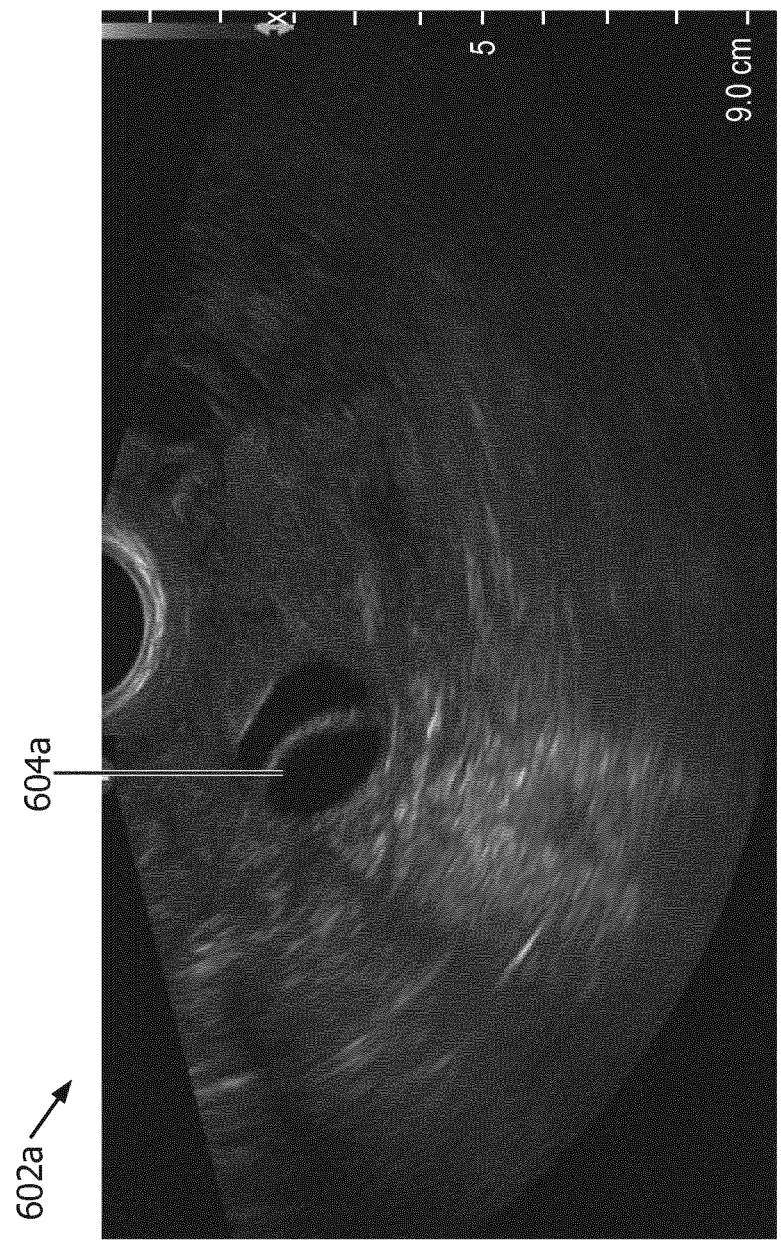
FIG. 6A is a photograph of an ultrasound image of an ovarian follicle that has not been pre-processed in accordance with principles of the present invention.

FIG. 6A is a photograph of an ultrasound image 602a of an ovarian follicle 604a that has not been pre-processed in accordance with principles of the present invention. As shown, the follicle 604a may appear darker than the surrounding pixels in the image before pre-processing. The follicle 604a may be difficult to consistently identify via a neural network when depicted in this manner, especially in ultrasound images that contain larger amounts of dark pixels and/or dark pixels located in close proximity with the ovarian follicle(s).

Figure 6B:
FIG. 6B is a photograph of an ultrasound image of an ovarian follicle that has been pre-processed in accordance with principles of the present invention.

FIG. 6B is a photograph of an ultrasound image 602b of the same ovarian follicle captured in the image shown in FIG. 6A, except the image has been pre-processed to produce an enhanced image of ovarian follicle 604b. During pre-processing, a brightness threshold was applied to the original ultrasound image 602a. All image pixels falling below the applied brightness threshold were assigned a zero value and inverted to white, and all image pixels falling above the threshold were inverted to black. Because the original image of the ovarian follicle 604a was nearly black, the pixels comprising the follicle fell below the brightness threshold, prompting one or more processors analyzing the image to invert the pixels to white. As a result, the ovarian follicle 604b contrasts sharply with the surrounding features captured in the pre-processed image 602b, enabling reliable, real-time detection of the follicles by a neural network on a point-of-care system.

Figure 7:
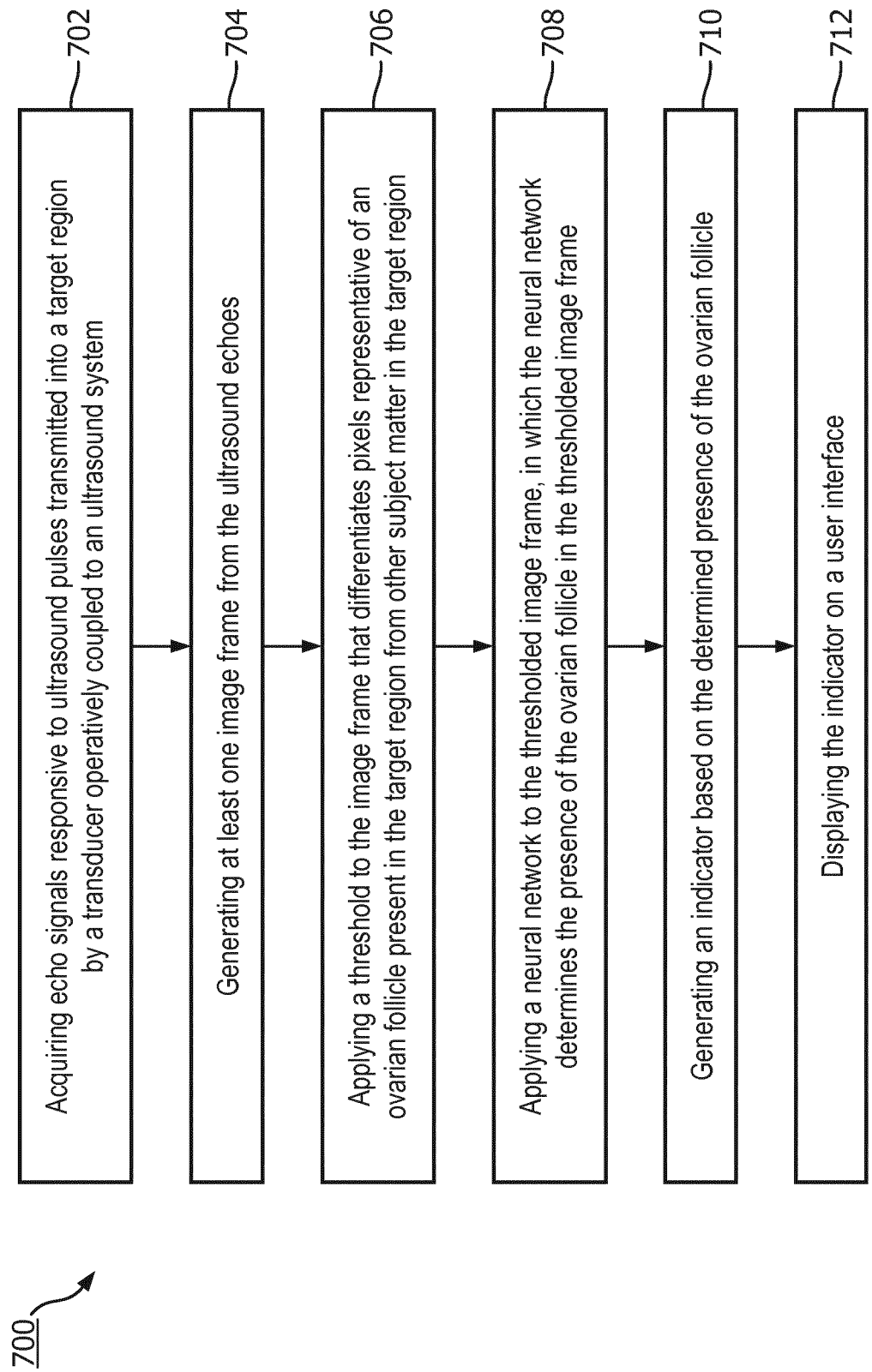
FIG. 7 is a flow diagram of a method of ultrasound imaging performed in accordance with principles of the present inventions.

FIG. 7 is a block diagram of an ultrasound imaging method in accordance with the principles of the present disclosure. The example method 700 of FIG. 7 shows the steps that may be utilized, in any sequence, by the systems and/or apparatuses described herein for identifying ovarian follicles during an ultrasound scan, which may be performed by a novice user via instructions provided in real time by the systems and/or apparatuses. The method 700 may be performed by an ultrasound imaging system, such as system 700, or other systems including, for example, a mobile system such as LUMIFY® by Koninklijke Philips N. V. ("Philips"). Additional example systems may include SPARQ® and/or EPIQ®, also produced by Philips.

In the embodiment shown, the method 700 begins at block 702 by "acquiring echo signals responsive to ultrasound pulses transmitted into a target region by a transducer operatively coupled to an ultrasound system." Echo signals may be gathered via an ultrasound data acquisition unit, which may contain various configurations of sensor arrays and components, such as those described above with respect to FIG. 1. In some examples, the ultrasound data acquisition unit may be portable and have a hand-held ultrasound probe manipulable by a user. The ultrasound probe may include a user interface and/or may be coupled to a desktop computer, portable laptop, or smartphone. The user may lack formal training in ultrasound operation.

At block 704, the method involves "generating at least one image frame from the ultrasound echoes." The image frame may be generated using one or more processors. In some examples, discrete signal processors and data processors may be included.

At block 706, the method involves "applying a threshold to the image frame that differentiates pixels representative of an ovarian follicle present in the target region from other subject matter in the target region." In some examples, the color or brightness of the differentiated pixels in the thresholded image frame can be inverted.

At block 708, the method involves "applying a neural network to the thresholded image frame, in which the neural network determines the presence of the ovarian follicle in the thresholded image frame." In some examples, the neural network is a convolutional neural network. The neural network may be trained using ultrasound images containing an ovary.

At block 710, the method involves "generating an indicator based on the determined presence of the ovarian follicle." In some examples, the indicator can be updated in real time in response to movement of the transducer. The indicator can be a binary, on-or-off indicator, or the indicator can gradually change based on the number of ovarian follicles detected, for example.

At block 712, the method involves "displaying the indicator on a user interface." In some examples, the method can further involve generating and displaying an ultrasound image from the thresholded image frame on the user interface. According to such examples, the indicator may be displayed adjacent to, or superimposed on, the ultrasound image. Embodiments may further involve sending ultrasound images to a specialist, such as a clinician. The specialist may be located at a remote location with respect to the location that the scan is being performed.

In various embodiments where components, systems and/ or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
an ultrasound transducer configured to acquire echo signals responsive to ultrasound pulses transmitted toward a target region;
one or more processors in communication with the ultrasound transducer and configured to:
generate an image frame from the echo signals;
apply a threshold to the image frame that differentiates pixels representative of an ovarian follicle present in the target region from other subject matter in the target region, the applying the threshold including modifying one or more of the pixels based on the threshold to increase a contrast of the image frame;
wherein the threshold is an Otsu threshold, and wherein the applying the threshold includes inverting a color of the pixels below and above the Otsu threshold to intensify an appearance of the ovarian follicle in the thresholded image frame;
apply a neural network to the thresholded image frame, in which the neural network determines if the ovarian follicle is present in the thresholded image frame;
generate a first indicator based on a determination that the ovarian follicle is present within the thresholded image frame, wherein the first indicator represents that the ovarian follicle is present within the thresholded image frame;
generate a different, second indicator based on a determination that the ovarian follicle is not present within the thresholded image frame, wherein the second indicator represents that the ovarian follicle is not present within the thresholded image frame;
generate a user instruction representing guidance to a user for positioning the ultrasound transducer such that the user instruction is different from the first indicator and the second indicator;
simultaneously display the first indicator and the image frame on a user interface in communication with the one or more processors in response to the determination that the ovarian follicle is present;
simultaneously display the second indicator and the image frame on the user interface in response to the determination that the ovarian follicle is not present; and
display the user instruction on the user interface.

2. The ultrasound imaging system of claim 1, wherein the user instruction is configured to guide the user through an ultrasound scan in response to at least one of the first indicator or the second indicator.

3. The ultrasound imaging system of claim 1, wherein the user instruction comprises at least one sensory cue different from the user interface displaying the user instruction.

4. The ultrasound imaging system of claim 1, wherein the user interface is configured to send the image frame to a remote receiver.

5. The ultrasound imaging system of claim 1, wherein the neural network comprises a deep neural network (DNN) or a convolutional neural network (CNN).

6. The ultrasound imaging system of claim 1, wherein the neural network comprises a convolutional neural network (CNN) comprised of one or more convnet layers and one or more fully connected layers.

7. The ultrasound imaging system of claim 1, wherein the neural network is operatively associated with a training algorithm configured to receive an array of training inputs and known outputs, wherein the training inputs comprise ovarian ultrasound image frames, and the known outputs comprise ovarian ultrasound image frames comprising an ovarian follicle.

8. The ultrasound imaging system of claim 1, wherein the neural network is implemented, at least in part, in a computer-readable medium comprising executable instructions, which when executed by the processors coupled to the ultrasound transducer, cause the processors to perform a machine-trained algorithm to produce at least one of the first indicator or the second indicator based on the acquired echo signals.

9. The ultrasound imaging system of claim 1,
wherein the first indicator is spaced from the image frame in the user interface, and
wherein the second indicator is spaced from the image frame in the user interface.

10. The ultrasound imaging system of claim 1, wherein the first indicator and the second indicator comprise a same shape.

11. The ultrasound imaging system of claim 10, wherein the first indicator comprises a first visual characteristic and the second indicator comprises a second visual characteristic different from the first visual characteristic.

12. A method of ultrasound imaging, the method comprising:
acquiring echo signals responsive to ultrasound pulses transmitted into a target region by a transducer operatively coupled to an ultrasound system;
generating an image frame from the echo signals;
applying a threshold to the image frame that differentiates pixels representative of an ovarian follicle present in the target region from other subject matter in the target region, the applying the threshold including modifying one or more of the pixels based on the threshold to increase a contrast of the image frame;
wherein the threshold is an Otsu threshold, and wherein the applying the threshold includes inverting a color of the pixels below and above the Otsu threshold to intensify an appearance of the ovarian follicle in the thresholded image frame;
applying a neural network to the thresholded image frame, in which the neural network determines if the ovarian follicle is present in the thresholded image frame;
generating a first indicator based on a determination that the ovarian follicle is present within the thresholded image frame, wherein the first indicator represents that the ovarian follicle is present within the thresholded image frame;
generating a different, second indicator based on a determination that the ovarian follicle is not present within the thresholded image frame, wherein the second indicator represents that the ovarian follicle is not present within the thresholded image frame;
generating a user instruction representing guidance to a user for positioning the ultrasound transducer such that the user instruction is different from the first indicator and the second indicator;

simultaneously displaying the first indicator and the image frame on a user interface in response to the determination that the ovarian follicle is present;

simultaneously displaying the second indicator and the image frame on the user interface in response to the determination that the ovarian follicle is not present; and displaying the user instruction on the user interface.

13. The method of claim 12, wherein the applying the threshold includes inverting a color of the pixels falling above and below the threshold.

14. The method of claim 12, wherein the user instruction comprises guidance for performing an ultrasound scan of an ovary responsive to at least one of the first indicator or the second indicator.

15. The method of claim 12, wherein the neural network comprises a convolutional neural network (CNN).

16. The method of claim 12, further comprising training the neural network using ultrasound image frames containing an ovary.

17. The method of claim 12, further comprising sending the image frame to a clinician, wherein the clinician is located at a remote location.

18. The method of claim 12, wherein at least one of the first indicator or the second indicator is updated in real time in response to movement of the transducer.

19. A non-transitory computer-readable medium comprising executable instructions, which when executed cause a processor of a medical imaging system to perform the method of claim 12.

* * * * *